(12) United States Patent
Lin

(10) Patent No.: US 8,006,702 B2
(45) Date of Patent: *Aug. 30, 2011

(54) SELECTIVE PHOTOCOAGULATION

(75) Inventor: Charles P Lin, Arlington, MA (US)

(73) Assignee: The General Hospital Corporation, Boston, MA (US)

(*) Notice: Subject to any disclaimer, the term of this patent is extended or adjusted under 35 U.S.C. 154(b) by 66 days.

This patent is subject to a terminal disclaimer.

(21) Appl. No.: 12/131,612

(22) Filed: Jun. 2, 2008

(65) Prior Publication Data

US 2008/0259422 A1 Oct. 23, 2008

Related U.S. Application Data

(60) Division of application No. 11/428,018, filed on Jul. 26, 2006, now Pat. No. 7,763,017, which is a continuation of application No. 10/296,417, filed as application No. PCT/US01/17818 on Jun. 1, 2001, now Pat. No. 7,115,120.

(60) Provisional application No. 60/209,010, filed on Jun. 1, 2000.

(51) Int. Cl.
*A61B 19/00* (2006.01)

(52) U.S. Cl. .................. 128/898; 606/4; 606/6; 607/88; 607/89

(58) Field of Classification Search .................. 607/88, 607/89; 606/4–6; 128/898

See application file for complete search history.

(56) References Cited

U.S. PATENT DOCUMENTS

| 4,644,948 A | 2/1987 | Lang et al. |
| 4,758,081 A | 7/1988 | Barnes |
| 5,029,220 A | 7/1991 | Juday |
| 5,254,112 A | 10/1993 | Sinofsky et al. |
| 5,302,259 A | 4/1994 | Birngruber |
| 5,459,570 A | 10/1995 | Swanson et al. |
| 5,549,596 A | 8/1996 | Latina |
| 5,549,599 A | 8/1996 | Sumiya |
| 5,620,437 A | 4/1997 | Sumiya |
| 5,778,133 A | 7/1998 | Plesko |
| 5,782,822 A | 7/1998 | Telfair et al. |
| 5,997,141 A * | 12/1999 | Heacock ................ 351/221 |
| 6,099,522 A * | 8/2000 | Knopp et al. ............ 606/10 |

(Continued)

FOREIGN PATENT DOCUMENTS

WO  99/65431  12/1999

OTHER PUBLICATIONS

Kelly et al., "Microcavitation and Cell Injury in RPE Cells Following Short-Pulsed Laser Irradiation", *SPIE* 2975:174-179 (1997).
Lin et al., "Selective Cell Killing by Microparticle Absorption of Pulsed Laser Radiation", *IEEE J. Sel. Topics Quantum Elect.* 5(4):963-968 (1999).

(Continued)

*Primary Examiner* — Ahmed M Farah
(74) *Attorney, Agent, or Firm* — Fish & Richardson P.C.

(57) ABSTRACT

A method of scanning a laser beam across a set of cells includes during a first interval, scanning a laser beam across a set of cells; and during a second interval, deflecting the laser beam away from the set of cells. The first interval is selected to cause microcavitation in at least a portion of the cells from the set of cells.

22 Claims, 2 Drawing Sheets

U.S. PATENT DOCUMENTS

| | | |
|---|---|---|
| 6,110,165 A | 8/2000 | Ota |
| 6,319,274 B1 * | 11/2001 | Shadduck .................. 607/89 |
| 6,428,532 B1 | 8/2002 | Doukas et al. |
| 6,610,051 B2 | 8/2003 | Bille |
| 6,671,043 B1 | 12/2003 | Huettman |
| 6,706,036 B2 * | 3/2004 | Lai .................. 606/12 |
| 6,743,221 B1 | 6/2004 | Hobart et al. |
| 6,887,232 B2 | 5/2005 | Bille |
| 2004/0102765 A1 | 5/2004 | Koenig |
| 2004/0176752 A1 | 9/2004 | Alfano et al. |
| 2005/0021013 A1 | 1/2005 | Visuri et al. |
| 2005/0197655 A1 | 9/2005 | Telfair et al. |

OTHER PUBLICATIONS

Vogel et al., "Cavitation bubble dynamics and acoustic transient generation in ocular surgery with pulsed neodymium: YAG lasers." *Ophthalmology*; vol. 93, No. 10, pp. 1259-1269, Oct. 1986.

Juhasz et al., "Time-resolved observations of shock waves and cavitation bubbles generated by femtosecond laser pulses in corneal tissue and water." *Lasers in Surgery and Medicine*, vol. 19, No. 1, pp. 23-31, Jan. 1996.

\* cited by examiner

SELECTIVE PHOTOCOAGULATION

CROSS-REFERENCE TO RELATED APPLICATION

This application is a divisional of U.S. application Ser. No. 11/428,018, filed Jun. 30, 2006, which is a continuation of U.S. application Ser. No. 10/296,417, filed Jul. 9, 2003, which is the U.S. national stage of PCT Application No. US01/17818, filed Jun. 1, 2001, which claims the benefit of U.S. Provisional Application Ser. No. 60/209,010, filed Jun. 1, 2000. The contents of all the foregoing applications are incorporated herein by this reference.

STATEMENT OF GOVERNMENTAL SUPPORT

This invention was made with Government support under Grant Nos. F49620-96-1-0241 and F49620-00-1-0179 awarded by the United States Air Force Office of Scientific Research and Grant No. EY012970 awarded by the National Institutes of Health. The Government has certain rights in this invention.

FIELD OF INVENTION

This invention relates to methods and devices useful in laser surgical techniques. More particularly, the invention relates to methods of determining therapeutic end points and preventing collateral damage in laser surgical techniques.

BACKGROUND

Laser surgery has become a generally useful technique, requiring specialized equipment and techniques. Laser surgery is indicated in the treatment of many eye diseases. For example, lasers are used to treat the ocular complications of diabetes. For glaucoma patients, lasers help to control the pressure inside the eye when medications alone do not succeed. Lasers are used to seal holes in the retina, and prevent or treat retinal detachments. Macular degeneration is another condition where lasers can sometimes help prevent vision loss. Laser surgery is also used after cataract surgery to improve vision, if necessary.

The retinal pigment epithelium (RPE) is a single cell layer, situated in the back of the eye behind a sensitive neuroretinal layer, with a high pigment density that can be targeted by laser irradiation. Retinal laser surgery can be classified into techniques which rely on thermal damage to the neuroretinal layer (such as retinal welding), and those that desirably do not involve damage to the neuroretinal layer (such as photocoagulative treatment of central serous retinopathy, diabetic macular edema, and drusen).

Conventional laser photocoagulation of the retina is performed with long pulses (on the order of from about 10 to about 500 ms) generated from a continuous wave laser, with the majority of the energy absorbed by the RPE. Heat diffusion during the long exposure to the laser pulse results in a relatively large zone of thermal damage, causing irreversible thermally-induced damage of not only the RPE cells, but also the photoreceptors and the choroicapillaris, producing scotomas (blind spots) in the treated areas.

Selective RPE photocoagulation is a recently developed therapeutic approach that uses short (microsecond) laser pulses to, ideally, target retinal pigment epithelial cells while not affecting adjacent photoreceptors in the retina, as described in U.S. Pat. No. 5,302,259 to Birngruber, and U.S. Pat. No. 5,549,596 to Latina. These treatment methods do not produce blind spots, as does conventional laser photocoagulation. In fact, these treatments do not produce any visible changes in the fundus during treatment. However, clinicians have to rely on post surgery fluorescein angiography to determine if the treatment endpoint has been reached, a procedure that requires approximately an hour and is inconvenient for the patient.

SUMMARY

The invention results from the discovery that detection of microbubbles within retinal pigment epithelial (RPE) cells formed upon absorption of pulsed laser radiation by RPE cells can be used to inhibit or prevent thermal and mechanical damage to cells proximate to those undergoing laser treatment. Thus, the invention allows substantially instantaneous control over the laser dosimetry to ensure that laser energy reaches the threshold required for RPE cell killing (a therapeutic endpoint), but avoids the administration of laser energies sufficient to damage adjacent cells, such as photoreceptors (collateral damage control).

As used herein, "microcavitation" refers to the sudden formation and collapse of microbubbles in a liquid, events which are primarily caused by the absorption of light by chromophores in the liquid. This term also applies to bubbles formed transiently by local heating. The term does not necessarily require pressure changes to exist.

In one aspect, the invention features a method of scanning a laser beam across a set of cells. The method includes, during a first interval, scanning a laser beam across a set of cells; and during a second interval, deflecting the laser beam away from the set of cells. The first interval is selected to cause microcavitation in at least a portion of the cells from the set of cells.

Some practices further include selecting the first interval to have a length that is about 40% of the length of the combined first and second intervals.

Other practices include causing the first interval to end upon detecting a selected extent of the microcavitation.

Additional practices include those in which scanning includes scanning at a scan rate between about 0.1 to about 10 microseconds per pixel, those in which scanning includes scanning at a scan rate between about 0.5 to about 7 microseconds per pixel, and those in which scanning includes scanning at a scan rate between about 1 to about 5 microseconds per pixel.

Other practices also include receiving a feedback signal indicative of microcavitation in the set of cells. In some of these practices, scanning is carried out at least in part on the basis of the feedback signal.

Additional practices include those in which scanning and deflecting both include modulating an acoustic-optical scanner, those in which scanning and deflecting both include rotating a polygonal mirror, those in which scanning and deflecting both include operating a galvometric scanner, and those in which scanning and deflecting both include operating a resonance scanner.

Additional practices include those in which the fluence of the laser beam is changed for a subsequence scan of the laser beam. These practices include those in which fluence is changed in response to a parameter of light scattered from the target cells. Exemplary parameters include those derived from or dependent on polarization, intensity, and/or Doppler shift of light scattered from target cells. As used herein, a parameter derived from, or dependent upon, a value of some property of the light includes the value itself.

In another aspect, the invention features an apparatus for scanning a laser beam across an array of cells. Such an apparatus includes a laser for providing a laser beam; a scanner disposed in the path of the laser beam; and a controller for causing the scanner to scan the laser beam across a cell array at a rate selected to cause microcavitation in the cell array.

In some embodiments, the controller is configured to cause the scanner to deflect the beam away from the cell array in response to detection of a selected extent of microcavitation within the cell array. In other embodiments, the controller is configured to cause the scanner to scan the laser beam across the cell array during a first interval and to deflect the laser beam away from the cell array during a second interval.

Other embodiments include those in which the controller is configured to cause the first interval to be about 40% of the sum of the combined first and second intervals, those in which the controller is configured to cause the scanner to scan the laser beam though an angle between about 0.1 degrees and about 5 degrees, those in which the controller is configured to cause the scanner to scan at a rate of between about 0.1 microseconds per pixel to about 10 microseconds per pixel, those in which the controller is configured to cause the scanner to scan at a rate of between about 0.5 to about 7 microseconds per pixel, and those in which the controller is configured to cause the scanner to scan at a rate of between about 1 to about 5 microseconds per pixel.

Additional embodiments further include a detector for receiving a signal indicative of microcavitation in the cell array.

In other embodiments, the controller is configured to control the scanner at least in part on the basis of a signal indicative of microcavitation in the cell array.

Embodiments also include those in which the scanner includes an acousto-optic scanner, those in which the scanner includes a polygonal mirror, those in which the scanner includes a galvometric scanner, and those in which the scanner includes a resonance scanner.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The present invention allows selective photocoagulation to be carried out without the need for an inconvenient post-operative determination of a therapeutic endpoint. The present invention allows the photocoagulation of RPE cells without complications and tissue destruction that can occur with conventional laser retinal surgery. The present invention provides an apparatus that is specifically suited for determination of a real-time therapeutic endpoint, and feedback based on this determination to minimize collateral damage which can arise from mechanical and thermal damage associated with photocoagulation therapies.

Other features and advantages of the invention will be apparent from the following detailed description, and from the claims.

DETAILED DESCRIPTION

The invention is based on the optical measurement of the onset of laser-induced cavitation and feedback to the laser source or to the operator to control the delivered laser energy based on the measurement. The absorption of laser energy by chromophores (specifically melanosomes) within, or proximate to, cells produces transient (lifetimes on the order of nanoseconds to microseconds) microcavitation bubbles with diameters on the order of micrometers. The bubbles arise since the laser excitation of the chromophores can rapidly produce local heating in the immediate vicinity of the chromophores. It has been observed that the local heating can be intense enough to vaporize a thin layer of liquid in intimate contact with the chromophores. Detection of the presence of microbubbles is a way to determine the amount of heating caused by laser energy. Microcavitation causes a temporary and measurable change in the reflectivity of the cells being irradiated. This change is used to adjust the energy of the laser source and thereby minimize damage to proximate cells that are not desirably exposed to the same laser energies used to cause photocoagulation or thermal energies that can kill those proximate cells.

Selective RPE photocoagulation with the feedback of the present invention provides useful therapeutic outcomes. While not bound by any particular theory of operation, it is believed that the selective killing of diseased RPE cells can stimulate neighboring RPE cells to proliferate and form a new and properly functional RPE cell layer to replace those killed by selective photocoagulation. Thus, selective RPE photocoagulation can serve as a method of treatment for diseases believed to be associated with the RPE, such as central serous retinopathy, diabetic macular edema, and drusen.

Figure 1:
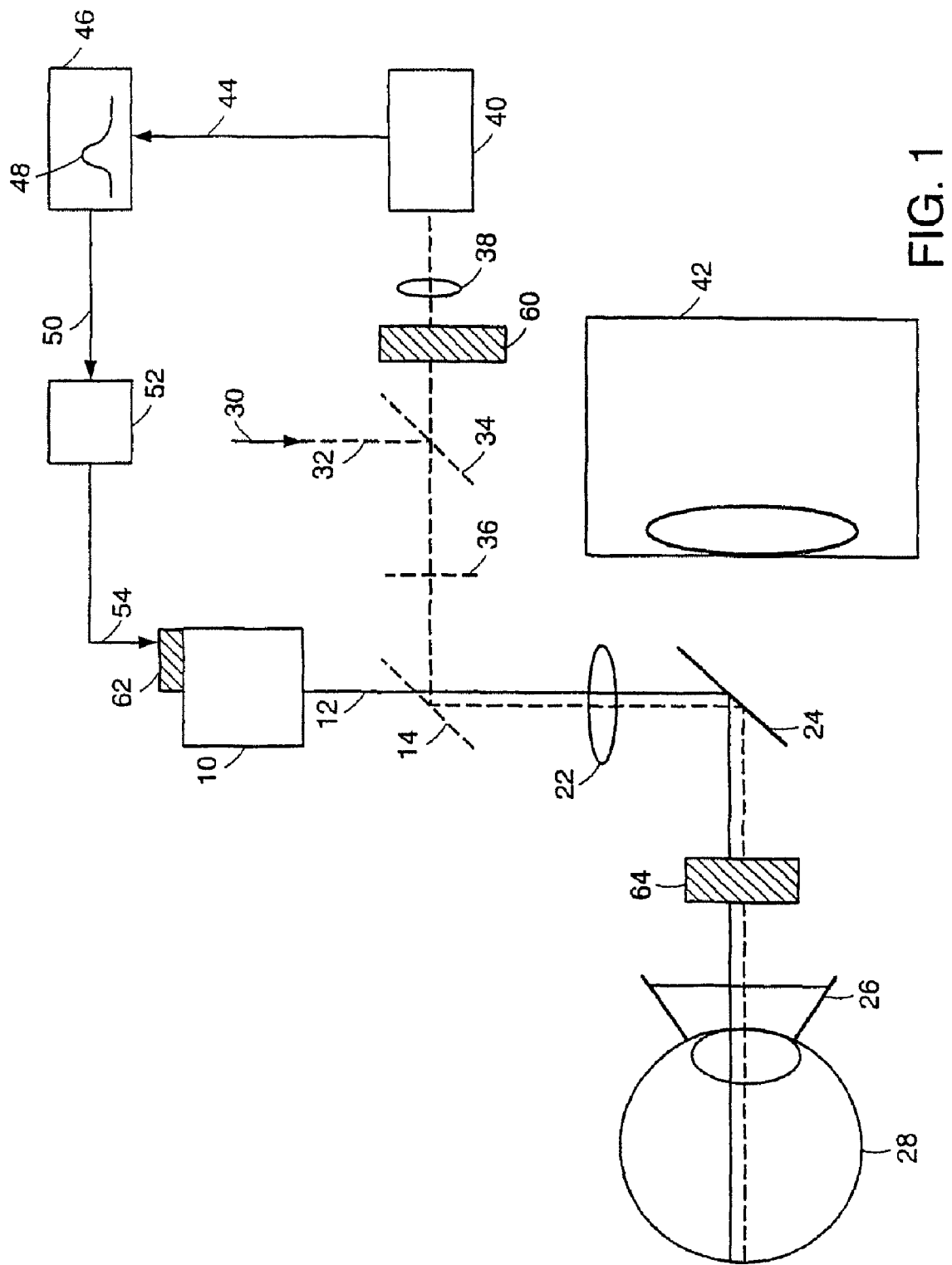
FIG. 1 is a schematic of a representative laser surgery system according to a particular embodiment of the invention.

Referring to FIG. 1, a representative laser surgery system is shown. Treatment laser source 10 sends treatment laser beam 12 to dichroic beam splitter 14. Dichroic beam splitter 14 is adapted to allow transmittance of treatment beam 12. Treatment beam 12 is focused by focusing lens 22 to impinge on mirror 24 that directs treatment beam 12 through contact lens 26 into eye 28. Scanner 64 can be used to controllably scan the electromagnetic radiation across the cells of eye 28. The position of scanner 64 is variable, and an illustrative example of a position is provided in FIG. 1. Optional probe laser 30 produces probe beam 32, which is directed onto polarizing beam splitter 34, directing probe beam 32 toward quarter wave plate 36. Probe beam 32 impinges on dichroic beam splitter 14, which is adapted to reflect probe beam 32 along substantially the same path as treatment beam 12. Probe beam 32 is reflected back along the same path and a fraction of probe beam 32 passes through polarizing filter 34, through focusing lens 38, and into detector 40. The probe laser and beam is optional. The interior of eye 28 is illuminated by slit lamp 42. Detector 40 sends detector signal 44 to discriminator 46 for determination of the presence of signal peak 48. Determination of the presence of signal peak 48 leads to signal 50 being sent to converter 52 which either sends signal 54 to laser source 10 immediately, or stores the current treatment laser energy value and, according to a multiplier value input to the converter, sends signal 54 to laser source 10 when the treatment laser energy reaches a value equal to the current treatment laser energy value plus some fraction of that value, determined by the multiplier value. Signal 54 can be a stop ramp signal, or can be a signal to input into controller 62, to modulate the electromagnetic radiation.

In some embodiments, interferometer 60 can be introduced between eye 28 and detector 40. In such embodiments, probe beam 32 (alternatively, treatment laser beam 12) is divided, so that a first portion of the beam impinges eye 28, and a second portion of the beam impinges interferometer 60. The position of interferometer 60 is variable, and an illustrative example of a position is shown in FIG. 1. Detector 40 operates to detect interference between these portions of the beam, for example frequency or intensity interferences.

Treatment Laser Source

The treatment laser source provides a treatment beam having the following characteristics. The wavelength of light (that is, the energy of light) of the treatment beam is chosen to be selectively absorbed by the target tissue. The wavelength of the light source is desirably within the absorption spectrum of the chromophore present within or proximate to the cell or group of cells to be treated. For example, a treatment laser that produces visible light can be used in the practice of the invention. Visible light is generally light having a wavelength of from about 400 nm to about 800 nm. For retinal pigment epithelial cells, preferred wavelengths for the treatment beam range from about 400 nm to about 600 nm, for example, from about 450 nm to about 550 nm.

For other medical procedures which can benefit from selective photocoagulation, such as treatment of neural tissue by laser surgery, other lasers can be utilized. For example, if a chromophoric material such as lamp black, or other laser light absorbing material, were delivered within, or bound to the surface of, tumor cells or other cells to be killed, the laser wavelength could be a longer wavelength light source tailored to the chromophoric material. The chromophore can be delivered to be absorbed within a cell, or can be bound to the surface of the cell, for example, by antibodies, or by covalent or ionic bonding. Chromophores which can be used in the practice of the invention can be any which will produce heat upon laser irradiation sufficient to create microbubbles, e.g., melanin, carbon black, gold, iron oxide, and other laser phototherapy chromophores known to those of skill in the art.

Light of significantly shorter wavelength than visible light can be absorbed directly by a wide variety of proteins, nucleotides, and many other cellular materials that tend to be distributed throughout cells generally. Thus, a treatment beam of a wavelength much shorter than 400 nm, for example, below 360 nm, does not tend to selectively affect cells containing visible-light chromophores, and thus should be avoided. Further, a treatment beam of significantly longer wavelength than visible light is not particularly strongly absorbed by the chromophores of the RPE, and therefore penetrates deeper into the choroid, effectively creating a thicker heat reservoir under the photoreceptors. This thicker heat reservoir takes longer to cool (since the cooling time increases as the square of the layer thickness), and releases more energy into the adjacent tissue. Thus, photoreceptors are more likely to be damaged with a treatment beam of near infrared wavelength, even if the pulse duration is shortened.

A laser which produces pulsed light can be used in the new methods. For example, pulses of pulse widths less than about 10 microseconds ($\mu s$) are desirable, for example less than about 5 $\mu s$, 1 $\mu s$, 100 nanoseconds (ns), 1 ns, or 100 picoseconds (ps). Pulse width (that is, pulse duration) of the laser is chosen to be sufficiently short that heat conduction away from the absorbing tissue to the surrounding tissue is minimized.

Alternatively, a laser that produces continuous light can be used. In such embodiments, the continuous light can be "chopped," for example, by an opto-acoustic modulator, which produces pulsed light. Such a chopper can be placed immediately in front of the laser source, so as to produce the same "chopped" light in both the through and reflected beam fractions.

In some embodiments, the laser energy is delivered to particular tissue areas, even to the limit of individual cells, as a train of short pulses. Each pulse within the train does not contain enough energy to cause mechanical disruption, but the effect of all short pulses cumulatively creates selective thermal damage at the RPE. Such trains are characterized, in part, by a repetition rate. In particular methods of treating tissue within the eye, the repetition rate is desirably high enough so that the pulse train be delivered to the tissue within less than about 1 second, so that the effects of eye movement can be minimized. On the other hand, the repetition rate is desirably not so high as to be substantially equivalent to continuous wave excitation, which can produce heating effects in the bulk tissue. The repetition rate varies from about 10 Hz to about 5000 Hz, for example, from about 50 Hz to about 2000 Hz, or from about 100 Hz to about 1000 Hz.

In traditional photocoagulation, with pulse widths of from about 50 to 500 ms, laser-tissue interaction is well described by thermal processes; absorption of light energy by the RPE is accompanied by heat diffusion away from the absorbing layer to the adjacent tissue, producing a zone of thermal damage which is visible under opthalmoscopic examination as a coagulated lesion on the retina. This thermal process remains for pulse widths down to the sub-millisecond range. For shorter pulse widths (ns and ps) on the other hand, very little thermal diffusion can take place on the timescale of the laser pulse. The laser energy is selectively deposited into the melanin granules within the RPE, creating a situation in which the temperature distribution in the cell is highly non-uniform. Discrete hot spots are created within the cell, at the energy absorbing granules, while the rest of the cell experiences little heating. Thermal diffusion creates temperature equilibrium on the timescale of microseconds after the laser pulse (for a melanosome of approximately 1 $\mu m$, the thermal relaxation takes place in approximately 1 $\mu s$). The average temperature of the whole cell after thermal relaxation is much lower than the initial temperature spikes created upon excitation. RPE killing is observed only when the laser fluence exceeds a threshold for initiating microscopic cavitation bubble formation inside the RPE cells. Transient heating alone below bubble formation does not appear to lead to cell killing.

Microbubbles originate from explosive vaporization of a thin (less than about 0.1 $\mu m$) layer of fluid surrounding the individual heated particles. The explosive growth of microbubbles is observed within less than a nanosecond after the particles are irradiated with a 30 picosecond laser pulse, but the bubbles are not stable. After an initial expansion to a maximum diameter of a few micrometers, the bubbles collapse with a lifetime of about 0.1 to 1 microsecond, the lifetime being fluence dependent. For fluences up to a few times the microcavitation threshold, coalescing bubbles can form from individual bubbles, and can collapse entirely within the cell, that is, the cell is not blown apart by the microexplosion. The cell retains its shape with little apparent change in morphology. Laser induced microcavitation is described generally in Kelly et al., "Microcavitation and cell injury in RPE cells following short-pulsed laser irradiation," Proc. SPIE 2975 (1997), and in Lin et al., "Selective Cell Killing by Microparticle Absorption of Pulsed Laser Radiation," IEEE J. Sel.Topics Quantum Elect., Vol. 5, No. 4, July/August 1999, pp 963-8.

At laser fluences of approximately five times the cavitation threshold, irradiated cells undergo a remarkable expansion which does not burst the cells, but distends them severely. At lower fluences, the bubbles are smaller, and the morphology of the cells changes very little after bubble collapse. Individual melanosomes also undergo cavitation in a similar manner. After bubble collapse, the melanosomes can remain intact.

A train of pulses with respect to particular areas of tissue can be produced by using a continuous wave laser and rapidly scanning the beam over the area of tissue, so that each RPE cell effectively is exposed only to a short pulse, such as a microsecond pulse. The cells or tissue to be treated can be repetitively exposed to such scans, to simulate multiple pulse exposures. Single pulses can produce unwanted mechanical perturbation of the cells or tissue being treated. The desired pulse width and repetition rate can be obtained by proper setting of the scanning speed (pixels/second) and scanning range. Scanning ranges can be any dimensions less than about 1000 μm× about 1000 μm, for example about 300 μm× about 300 μm. The scanning fields need not be square, but can be rectangular, or any shape convenient to scan. The scan lines need not be contiguous. Separated scan lines can further minimize thermal build-up in the bulk tissue. The exact dimensions will depend on the particular optics utilized in the surgical setup, as can be recognized and optimized by those of skill in the art.

In some embodiments, the laser beam is scanned by an opto-acoustic deflector, which can deflect a continuous wave laser. The continuous wave laser is able to remain "on" essentially 100% of the time. The scanning methodology can be defined by parameters of scanning speed and scan angle. Useful scanning speed can range from about 0.1 to about 10 μs per pixel, for example, from about 0.5 to about 7 μs per pixel, or from about 1 to about 5 μs per pixel. The scan angle can range from about 0.1 to about 5 degrees, for example, from about 0.5 to about 2 degrees.

Scanning can be carried out by a number of different scanning devices, such as two-dimensional acousto-optic deflectors (2D-AOD), galvometric scanners, rotating polygons, and resonance scanners. In some embodiments, acousto-optic deflectors are useful, because of their speed, linearity across the scan, and variable scan ranges, leading to more efficient data collection than is available with some other scanning devices. In addition, because 2D-AOD scanning uses sound waves in a crystal, there are no moving parts. Suitable AOD scanners are commercially available, for example, from Brimrose Corp. Suitable scanners include a two orthogonal AO crystals to scan the optical beam in x and y directions. Scanning can be carried up to 1.6 degrees on either axis, equivalent to a scan of 480 μm by 480 μm on the fundus of the eye if no contact lens is used.

Desirable laser fluences for selective photocoagulation are dependent on the detection of microcavitation, the particular pulse width for pulsed lasers or chopped beams, the wavelength of laser light employed, the type of cell irradiated, and the concentration of chromophore irradiated. For example, for treatment of RPE cells using 8 ns pulse widths of 532 nm light, the treatment laser fluences which are desirable range from about 0.08 to about 0.16 J/cm$^2$. For treatment of RPE cells using 3 μs pulse widths of 532 nm light, the treatment laser fluences which are desirable range from about 0.22 to about 0.44 J/cm$^2$.

Particular treatment lasers which can be used in the practice of the invention include continuous wave lasers, including gas lasers such as argon ion, krypton ion lasers adjusted to produce visible light, as well as solid state lasers which produce visible light, such as Nd-YAG lasers. A variety of excimer-pumped or YAG laser-pumped dye lasers can also be used to readily produce pulsed visible excitation. In some embodiments, the treatment laser source utilized is an Nd-YAG laser operating at 532 nm.

Probe/Detection

As shown in FIG. 1, the invention can also utilize a probe source that provides a probe beam. The wavelength of the probe beam can vary, but it should be recognized that generally, it is considered desirable to filter the generally intense treatment laser beam so that it does not saturate the detector, and that filter means are generally not extremely selective, so that spectral information in the immediate wavelength vicinity of the treatment beam may not be available for monitoring. Therefore, it may be preferable to use probe source which can illuminate in spectral regions somewhat removed from the treatment source wavelength, for example, at least about 3 nm, 5 nm, or 7 nm away.

Detection of bubbles formed with a scanning excitation laser beam can be done with the probe beam scanned together with the excitation beam. Alternatively, the probe beam can be left stationary somewhere within the scanning field, for example near the center of the scanning field. In such a configuration, the stationary probe beam will detect a bubble only when the excitation beam imparts enough energy to the spot covered by the probe beam to produce a bubble, giving rise to a time-dependent signal synchronized with the scan. Alternatively, back-scattering of the excitation beam itself can be used to monitor bubble formation. In such a configuration, the back-scattering intensity is detected by a detector and compared with a reference intensity generated from the excitation beam itself. Below the bubble formation threshold, the back-scattering signal will be proportional to the reference intensity, with some variation as the beam scans over the treatment area. Above the bubble formation threshold, the back-scattering signal will be enhanced and show much greater fluctuation due to the expansion and collapse of bubbles. The increase in light fluctuation can be used as a signature for the onset of bubble formation.

The intensity of the probe beam must be sufficient to allow monitoring of the transient events within the cell or tissue of interest. The optical properties of the sample can dictate the intensity considerations for the probe source. On the other hand, the intensity should not be so great as to independently cause heating within the cell or tissue. The adjustment of the intensity of the probe source to meet these criteria is within the capabilities of one of ordinary skill in the art.

The particular absorbance and reflectance properties can dictate the geometry of the probe and detection instruments. Any geometry which allows detection of scattered light can be used. In particular embodiments, the probe source can be used in a through-sample or reflective (back-scattering) geometry. For in vivo applications, through-sample will not generally be possible. Back-scattering geometries are generally more useful for in vivo treatment. In some embodiments, the geometry is a back-scattering detection of an optical probe beam. For example a helium neon (HeNe) laser can be focused to a 10 μm diameter spot on the tissue to be treated. The probe laser power should be adjusted to prevent heating of the tissue by the probe beam, and can be from about 0.01 to about 1 mW, for example, from about 0.05 to about 1 mW, or from about 0.1 to about 1 mW.

The probe beam can be continuous wave or pulsed. If the probe beam is pulsed, and the treatment beam is scanned, the probe beam is desirably synchronized with the treatment beam to improve signal quality.

Detection of an optical probe can be accomplished by photodiodes, photomultiplier tubes (PMT), and other similar and associated devices known in the art. The various advantages and capabilities of optical detection systems are discussed in numerous references known to those of skill in the art. For the present purposes, important capabilities of an optical detection system are speed and sensitivity. In particular embodiments, an avalanche-type photodiode can be used, with a confocal aperture placed in front of the opening. Bandpass filters can be employed to substantially eliminate the signal from reaching the detector and overloading or possibly damaging the detector.

The output of the detector is fed into a monitoring device, such as an oscilloscope, a cathode ray-type monitor, a pen recorder, or other monitoring device. In particular embodiments, the output of the detector is fed into a digital oscilloscope, which is synchronously triggered by the laser source producing the excitation beam.

Methods of Treatment

The invention includes methods of treating tissue by killing cells, individually and in groups. These methods are carried out by administering laser energy sufficient to photocoagulate the cells within particular tissue, or regions of tissue, while avoiding harm to adjacent or neighboring tissue, or regions of tissue. These methods involve the formation of microbubbles within the individual target cells or groups of target cells, but without allowing heat transfer sufficient to cause significant damage to cells proximate the target cells. Bubble formation is used as a treatment endpoint monitor. Even if bubble formation occurs at a fluence above the threshold for RPE cell killing, it can still be used to mark the treatment endpoint as long as the degree of tissue damage at this fluence is well confined to the RPE and spares the photoreceptors.

For example, methods of treating particular cells in RPE tissue involve exercising substantially precise control over the laser dosimetry administered. Such control is achieved by a real-time monitor that reflects the state of affairs within the tissue being treated. The control is based on the use of microbubble detection to determine the end-point of laser therapy for target cells, and to prevent damage to cells proximate the target cells.

As a first step to carry out therapeutic treatment involving the inventive method, target cells are identified. Target cells can be any which can benefit from selective photocoagulation treatment. Target cells must be able to absorb laser energy selectively, or be treated to be able to absorb laser energy selectively (e.g., by the introduction of a chromophore). Suitable target cells for selective photocoagulation are those target cells which are proximate to cells which should not be photocoagulated. For example, retinal pigment epithelial cells, which are proximate to neuroretinal cells, are well suited for selective photocoagulation. Brain tumor cells, which are proximate to normally functioning cells, can also be target cells. Target cells are prepared for exposure to a treatment laser beam by positioning focusing optics, such as a contact lens for RPE cell treatment. The application of a contact lens for laser eye surgery is well known to those of skill in the art. The treatment laser is activated to operate initially at a low beam intensity, for example, from about 10% to about 80%, for example, from about 25% to about 80%, or from about 50% to about 75%, of the $ED_{50}$ threshold determined for a particular pulse width and cell type. For example, for selective RPE photocoagulation, the laser can be initially operated at beam fluences of from about 0.008 to about 0.064 J/cm$^2$, for an 8 ns pulse width, or from about 0.022 to about 0.176 J/cm$^2$ for a 3 μs pulse. The laser beam fluence can be slowly increased while monitoring parameters of the scattered treatment beam, as determined from a back-scattering geometry, for example. One useful parameter is the intensity of the treatment beam scattered from target cells. Other useful parameters can be polarization of light scattered from target cells, or Doppler shifts of light scattered from target cells, which arise due to the expansion and other movement of microbubbles.

The monitoring should be carried out so as to determine if there is any change, for example, a positive change, in the reflectivity of the target cells. As used in this context, a "change" refers to a difference in signal which is detectable by a sustained change in the slope in a plot of target cell reflectance versus time, by a sustained change in relative target cell reflectance signal as compared to a baseline reflectance, or by observation of a visually apparent peak in a plot of target cell reflectance versus time. In embodiments which monitor changes in a scanning treatment beam, the background reflectance may fluctuate as the treatment beam passes over the relatively inhomogeneous surfaces of target cells, which can include structures such as blood vessels, which can show changes in reflectivity even in the absence of bubble formation. The formation of microbubbles is expected to be discernable over this fluctuating background, so that peaks due to bubble formation may be somewhat more difficult to detect, but not prohibitively difficult. The detection of microbubbles correlates with the laser beam energy which is referred to as $ED_{50}$, that is the laser dose necessary to result in death of 50% of target cells.

Upon detection of a change in reflectivity, by digital, analog, or manual means, the treatment laser beam intensity can be immediately or subsequently modulated, that is, by discontinuing the increase in treatment laser beam energy. In some embodiments, the detection of microbubbles signifies an immediate or substantially immediate halt in the ramp of beam intensity increase. In some embodiments, the detection of microbubbles will cause the beam intensity to be noted, as a digital or analog value (as a threshold value, that is $ED_{50}$) and the ramp of beam intensity will be continued until a value of $ED_{50}+xED_{50}$ is reached, where x is greater than zero, and less than about two.

Bubble formation can form near the end of the laser pulse, if the laser energy is initially selected to be low relative to the bubble formation threshold, and gradually increased to reach this threshold. Therefore, the back-scattered signal intensity should show a sudden increase near the end of the laser pulse if a bubble is produced. By comparing the incoming pulse shape with the scattered pulse shape, the onset of bubble formation can be determined.

Particular diseases in the retina are associated with retinal pigment epithelium. The RPE has as a primary function the exchange of nutrients to and from neuroretinal and other cells. These diseases include, for example, central serous retinopathy, diabetic macular edema, and drusen. The invention provides a means of treatment of such diseases by selective RPE photocoagulation.

EXAMPLES

The following examples illustrate certain properties and advantages inherent in some particular embodiments of the invention.

Example 1

Ex Vivo Transient Bubble Formation

Porcine eyes of approximately 20 mm diameter were prepared 0 to 4 hours after enucleation. The eyes were dissected, and the vitreous was removed. A sheet of 1 cm$^2$ was cut out of the equatorial region of the eye and the sample was suspended in 0.9% saline solution. After 20 minutes the retina could be easily peeled off. The sample was flattened at the edges using a plastic ring. The RPE was covered with diluted CalceinAM (Molecular Probes) 1:1000 in PBS or Dulbecos modified eagle medium (Gibco). A cover slip was applied on top. After 20 minutes, viable cells accumulated enough fluorescent Calcein to be distinguished from dead cells by fluorescence microscopy. Calcein fluorescence was excited at 488 nm and detected from 540 nm to 800 nm. One fluorescence image was taken before and a second 15-30 minutes after irradiation. Non-fluorescing cells where classified as dead. For 12 ns experiments, the sample temperature was 20° C. For 6 µs pulses, the sample was kept at 35° C. The thresholds were calculated using a PC program for probit analyses (Cain et al., "A Comparison of Various Probit Methods for Analyzing Yes/No Data on a Log Scale," US Air Force Armstrong Laboratory, AL/OE-TR-1996-0102, 1996) after Finney ("Probit Analysis," 3rd ed. London: Cambridge University Press; 1971).

A 20× objective (NA 0.42, 25 mm working distance) was used to image the cells onto a CCD camera. The spatial resolution of the setup was approximately 1 µm. A frequency-doubled, Nd:YAG Laser (Continuum, SEO 1-2-3, $\lambda$=532 nm, 6 mm beam) was used for 12 ns irradiation. A 200 µm section from the center of the beam was imaged on the sample to give a flat top image of 20 µm diameter. The intensity variations at the sample due to hot spots in the beam were below 15%, as determined by a fluorescing target within the area of irradiation. 6 µs Pulses were chopped from a cw frequency doubled Nd:YAG Laser (Verdi, Coherent, $\lambda$=532 nm). The Gaussian-shaped spot had FWHM of 16 µm on the sample. To probe the bubble formation, the collimated beam of a diode laser (SF830S-18, Microlaser Systems, 830 nm, 1.5×2 mm beam diameter) was focused (7×10 µm FWHM) onto the RPE cell with a maximum power of 1 mW at the sample. The average Nd:YAG power was 75 mW. The probe beam was switched on for less then 10 µs and switched off (1% power) 2-4 µs after the end of the pulse. The light was detected in a confocal geometry and also slightly off the optical axis to reduce back reflectance and scattering from the optical system and from tissue layers other than the RPE. The detector used was an avalanche photodiode (Hamamatsu C-5460), including a high-speed amplifier with 10 MHz bandwidth.

For 12 ns pulses, 4 samples from 4 different eyes were taken, on which a total of 117 spots were irradiated at different fluences (40 controls with Nd:YAG only, 77 including probe beam). The threshold for cavitation and cell death were the same, as displayed in Table 1. FLL refers to the fluence lower threshold level, FUL is the fluence upper threshold level, and Fluence is the mean of these two determinations. The # cells is the number of cells exposed to irradiation.

TABLE 1

12 Nanosecond Thresholds for Cavitation and Cell Death

| | Fluence (mJ/cm$^2$) | FLL Fluence (mJ/cm$^2$) | FUL Fluence (mJ/cm$^2$) | slope | # cells |
|---|---|---|---|---|---|
| cell death | 71 | 66 | 75 | 17 | 77 |
| cavitation | 71 | 67 | 75 | 16 | 77 |
| control | 71 | 66 | 81 | 14 | 40 |

Figure 2:
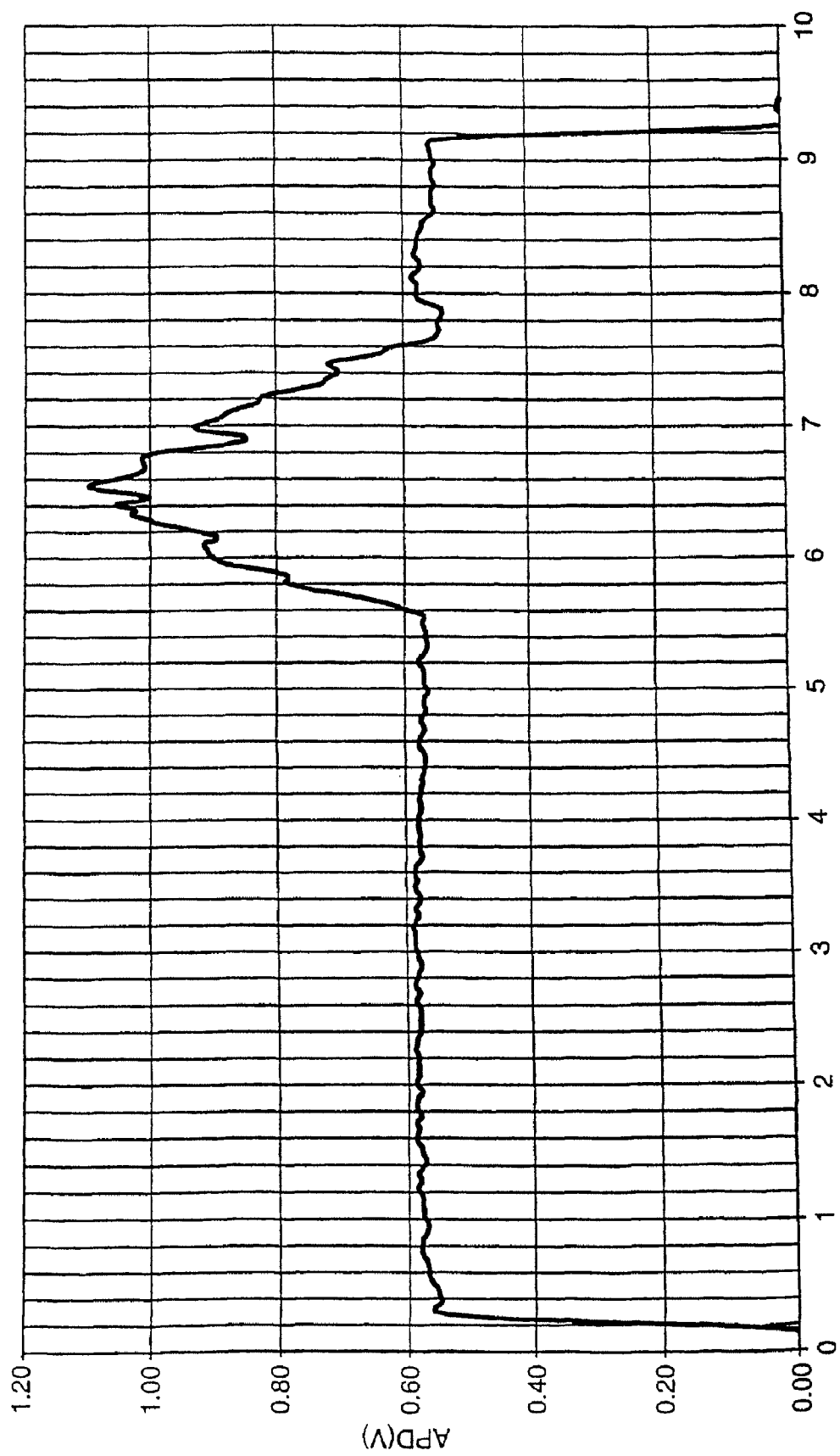
FIG. 2 is an oscilloscope trace of reflectivity versus time.

FIG. 2 is an oscilloscope trace of a reflectance signal at 1.1 times threshold with a minimal lifetime of 200 ns. The diode laser was switched on at 0.2 µs and switched off at +3.4 As to minimize sample heating. The Nd:YAG laser was fired at 1.2 µs, which caused a detectable increase in probe beam back scattering in a single RPE cell.

Example 2

In Vivo Treatment of RPE Tissue

A total of six eyes of three chinchilla gray rabbits are used. The rabbits are anesthetized with ketamine hydrochloride (30 mg/kg) and xylazine hydrochloride (6 mg/kg). The eyes are dilated with 1 drop of cyclopentolate hydrochloride and 1 drop of 5% phenylephrine hydrochloride, then a −67 diopter Goldmann planoconcave lens is placed on the eye.

For laser irradiation, the output of a Q-switch, frequency doubled Nd:YAG laser at a wavelength of 532 nm is used. The pulse width is controlled by shaping the high voltage pulse applied to the Pockel's cell while actively monitoring the intracavity energy build up. Without the active feedback, the normal Q-switch output pulse width is typically 250 ns with pulse energies of several mJ at a repetition rate of 500 Hz. A probe beam is provided by a HeNe laser at 0.5 mW. The back scattered probe beam is detected by an avalanche photodiode. The output of the detector is fed into an oscilloscope.

Under slitlamp examination, four 100 µm marker lesions are placed outside the corners of a designated 300 µm×300 µm treatment area, using 100 ms of continuous laser exposure each (approximately 100 mW). Then the treatment beam is turned on, and 100 successive scans are delivered to the treatment area. Each eye receives four such treatment spots with laser power settings of 0.5, 1, 2, and 3 times the $ED_{50}$ threshold as determined above. All laser treatment procedures are recorded with a CCD camera and a video tape recorder. Fundus imaging and fluorescein angiography is performed at 1 hour after irradiation. Changes in probe beam scattering are detected and displayed on the oscilloscope. The detection of microbubbles is accompanied by stabilization of laser fluence at 1.5 $ED_{50}$. Treatment is further carried out at this fluence.

At the completion of the treatment, the animals are sacrificed with pentobarbital injection. The eyes are enucleated and processed for light and electron microscopy examination. The total time from laser exposure to enucleation is approximately 2 hours. Each enucleated eye is fixed in phosphate-buffered 2% glutaraldehyde for 24 hours. The anterior segments and vitreous are removed, and the posterior eye is postfixed in phosphate-buffered 2% osmium tetroxide, dehydrated, and embedded in epoxy resin. Thick sections (approximately 1 µm) for light microscopy are stained with toluidine blue. Thin sections for electron microscopy are stained with uranyl acetate/lead acetate. Areas treated by the scanning laser are compared with control areas and with marker lesions (coagulated with continuous wave laser) for damage to the photoreceptors, RPE, Bruch's membrane, and the choriocapillaris. Comparison is made to verify that the RPE cells are photodamaged and the photoreceptors, Bruch's membrane, and the choriocapillaris are undamaged and viable.

Other Embodiments

It is to be understood that while the invention has been described in conjunction with the detailed description thereof, the forgoing description is intended to illustrate and not limit the scope of the invention, which is defined by the scope of the appended claims. Other aspects, advantages, and modifications are within the scope of the following claims:

The invention claimed is:

1. A method of photocoagulating cells, the method comprising:
   during a first interval, scanning a laser beam across a set of cells, wherein one or more laser parameters and a length of the first interval are selected to cause microcavitation in the set of cells;
   during a second interval, deflecting the laser beam away from the set of cells;
   detecting radiation from the set of cells;
   determining an extent of the microcavitation occurring in the set of cells based on the detected radiation; and
   ending the first interval and beginning the second interval after a selected extent of the microcavitation has occurred in the set of cells.

2. The method of claim 1, further comprising selecting the first interval to have a length that is about 40% of the length of the combined first and second intervals.

3. The method of claim 1, wherein scanning comprises scanning at a scan rate between about 0.1 to about 10 microseconds per pixel.

4. The method of claim 3, wherein scanning comprises scanning at a scan rate between about 0.5 to about 7 microseconds per pixel.

5. The method of claim 4, wherein scanning comprises scanning at a scan rate between about 1 to about 5 microseconds per pixel.

6. The method of claim 1, wherein the radiation from the set of cells forms a feedback signal indicative of microcavitation in the set of cells.

7. The method of claim 6, wherein scanning comprises scanning at least in part on the basis of the feedback signal.

8. The method of claim 1, wherein scanning and deflecting both comprise modulating an acoustic-optical scanner.

9. The method of claim 1, wherein scanning and deflecting both comprise rotating a polygonal mirror.

10. The method of claim 1, wherein scanning and deflecting both comprise operating a resonance scanner.

11. The method of claim 1, further comprising changing a fluence of the laser beam for a subsequent scan of the beam.

12. The method of claim 11, wherein changing the fluence comprises changing the fluence in response to a parameter of light scattered from the cells.

13. The method of claim 12, wherein changing the fluence in response to a parameter comprises changing the fluence in response to polarization of light scattered from the cells.

14. The method of claim 12, wherein changing the fluence in response to a parameter comprises changing the fluence in response to Doppler shift of light scattered from the cells.

15. The method of claim 12, wherein changing the fluence in response to a parameter comprises changing the fluence in response to the intensity of light scattered from the cells.

16. The method of claim 1, wherein the cells comprise retinal cells.

17. The method of claim 1, wherein the microcavitation comprises microbubble formation in the set of cells.

18. A method of treatment, comprising:
   using the method of claim 1 in treating at least one of glaucoma, ocular complications due to diabetes, macular degeneration, and retinal detachment in a patient.

19. A method of causing photocoagulation of cells, the method comprising:
   scanning a laser across a set of cells at a scanning frequency and laser power selected to cause microcavitation in the set of cells;
   detecting microcavitation in the set of cells; and
   terminating the scanning when a selected extent of microcavitation has occurred,
   wherein scanning the laser comprises:
      defining a first scan line;
      defining a second scan line;
      defining a third scan line disposed between the first and second scan lines;
      scanning the laser across the first scan line;
      skipping over the third scan line; and
      scanning the laser across the second scan line,
      whereby heat generated by scanning across the first scan line dissipates into cells located along the third scan line.

20. The method of claim 19, wherein the cells comprise retinal cells.

21. The method of claim 19, wherein the microcavitation comprises microbubble formation in the subset of cells.

22. A method of treatment, comprising:
   using the method of claim 19 in treating at least one of glaucoma, ocular complications due to diabetes, macular degeneration, and retinal detachment in a patient.

* * * * *